United States Patent [19]

Tabak et al.

[11] 4,163,028
[45] Jul. 31, 1979

[54] XYLENE ISOMERIZATION

[75] Inventors: Samuel A. Tabak, Wenonah; Roger A. Morrison, West Deptford, both of N.J.

[73] Assignee: Mobil Oil Corporation, New York, N.Y.

[21] Appl. No.: 912,681

[22] Filed: Jun. 5, 1978

Related U.S. Application Data

[63] Continuation-in-part of Ser. No. 818,171, Jul. 22, 1977, abandoned.

[51] Int. Cl.² ............................................. C07C 5/24
[52] U.S. Cl. ................................... 585/481; 585/488; 585/486
[58] Field of Search ................................... 260/668 A

[56] References Cited

U.S. PATENT DOCUMENTS

| 3,856,871 | 12/1974 | Haag et al. | 260/668 A |
| 3,856,872 | 12/1974 | Morrison | 260/668 A |
| 3,856,873 | 12/1974 | Barress | 260/668 A |

Primary Examiner—Veronica O'Keefe
Attorney, Agent, or Firm—Charles A. Huggett; Raymond W. Barclay

[57] ABSTRACT

Isomerization of xylenes in admixture with ethyl benzene by contact with a zeolite catalyst such as ZSM-5 is improved by use of zeolite having a silica/alumina ratio of at least 500 at a temperature above about 800° F. At these conditions, conversion of ethyl benzene follows a different reaction path which permits high conversion of ethyl benzene to benzene without loss of xylenes by disproportionation.

13 Claims, 1 Drawing Figure

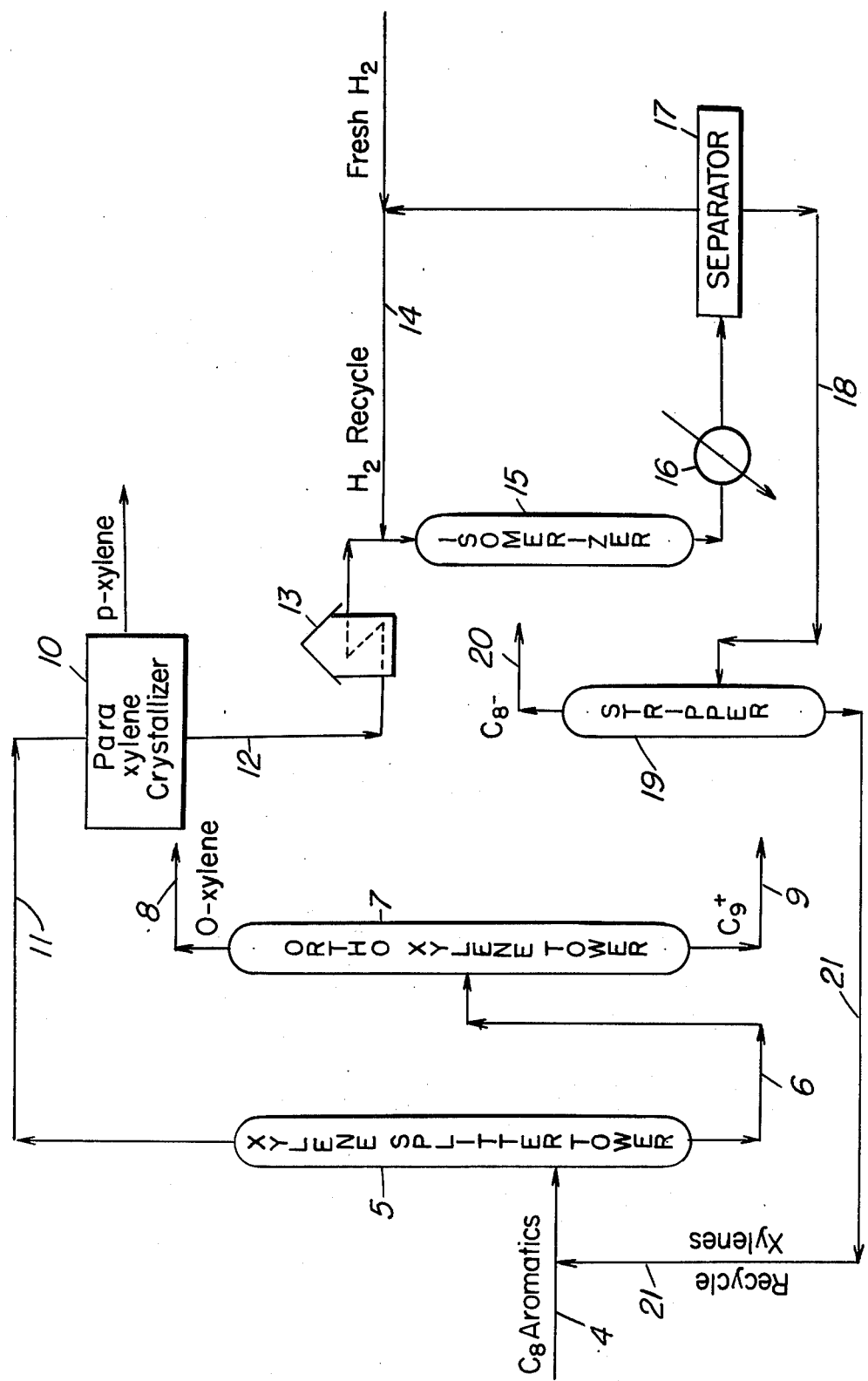

XYLENE ISOMERIZATION

CROSS-REFERENCE TO RELATED APPLICATIONS

This application is a continuation in part of copending application Ser. No. 818,171, filed July 22, 1977, now abandoned.

BACKGROUND OF THE INVENTION

Since the announcement of the first commercial installation of Octafining in Japan in June, 1958, this process has been widely installed for the supply of p-xylene. See "Advances in Petroleum Chemistry and Refining" volume 4 page 433 (Interscience Publishers, New York 1961). That demand for p-xylene has increased at remarkable rates, particularly because of the demand for terephthalic acid to be used in the manufacture of polyesters.

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

|  | Freezing Point °F. | Boiling Point °F. | Density lbs./U.S. Gal. |
|---|---|---|---|
| Ethyl benzene | −139.0 | 277.1 | 7.26 |
| P-xylene | 55.9 | 281.0 | 7.21 |
| M-xylene | −54.2 | 282.4 | 7.23 |
| O-xylene | −13.3 | 292.0 | 7.37 |
| W-M 23.92 | 3.72 ±0.06 |  |  |

Principal sources are catalytically reformed naphthas and pyrolysis distillates. The $C_8$ aromatic fractions from these sources vary quite widely in composition but will usually be in the range of 10 to 32 wt. % ethyl benzene with the balance, xylenes, being divided approximately 50 wt. % meta, and 25 wt. % each of para and ortho.

Individual isomer products may be separated from the naturally occurring mixtures by appropriate physical methods. Ethyl benzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes. At present, several xylene isomerization processes are available and in commercial use.

The isomerization process operates in conjunction with the product xylene or xylenes separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

It will be apparent that separation techniques for recovery of one or more xylene isomers will not have material effect on the ethyl benzene introduced with charge to the recovery isomerization "loop". That compound, normally present in eight carbon atom aromatic fractions, will accumulate in the loop unless excluded from the charge or converted by some reaction in the loop to products which are separable from xylenes by means tolerable in the loop. Ethyl benzene can be separated from the xylenes of boiling point near that of ethyl benzene by extremely expensive "superfractionation". This capital and operating expense cannot be tolerated in the loop where the high recycle rate would require an extremely large distillation unit for the purpose. It is a usual adjunct of low pressure, low temperature isomerization as a charge preparation facility in which ethyl benzene is separated from the virgin $C_8$ aromatic fraction before introduction to the loop.

Other isomerization processes operate at higher pressure and temperature, usually under hydrogen pressure in the presence of catalysts which convert ethyl benzene to products readily separated by relatively simple distillation in the loop, which distillation is needed in any event to separate by-products of xylene isomerization from the recycle stream. For example, the Octafining catalyst of platinum on a silicaalumina composite exhibits the dual functions of hydrogenation/dehydrogenation and isomerization.

Ethyl benzene reacts through ethyl cyclohexane to dimethyl cyclohexanes which in turn equilibrate to xylenes. Competing reactions are disproportionation of ethyl benzene to benzene and diethyl benzene, hydrocracking of ethyl benzene to ethylene and benzene and hydrocracking of the alkyl cyclohexanes.

The rate of ethyl benzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.) has but a very small effect on ethyl benzene approach to equilibrium.

Concurrent loss of ethyl benzene to other molecular weight products relates to % approach to equilibrium. Products formed from ethyl benzene include $C_6^+$ naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than does ethyl benzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethyl benzene has been found responsible for a relatively rapid decline in catalyst avtivity and this effect is proportional to its concentration in a $C_8$ aromatic feed mixture. It has been possible to relate catalyst stability (or loss in activity) to feed composition (ethyl benzene content and hydrogen recycle ratio) so that for any $C_8$ aromatic feed, desired xylene products can be made with a selected suitably long catalyst use cycle.

A different approach to conversion of ethyl benzene is described in Morrison U.S. Pat. No. 3,856,872, dated Dec. 24, 1974. Over an active acid catalyst typified by zeolite ZSM-5, ethyl benzene disproportionates to benzene and diethyl benzene which are readily separated from xylenes by the distillation equipment needed in the loop to remove by-products. It is recognized that rate of disproportionation of ethyl benzene is related to the rate of conversion of xylenes to other compounds, e.g. by disproportionation.

In the known processes for accepting ethyl benzene to the loop, conversion of that compound is constrained by the need to hold conversion of xylenes to an acceptable level. Thus, although the Morrison technique provides significant advantages over Octafining in this respect, operating conditions are still selected to balance the advantages of ethyl benzene conversion against the disadvantages of xylene loss by disproportionation and the like.

The present invention is predicated on discovery of a combination of catalyst and operating conditions which decouples ethyl benzene conversion from xylene loss in a xylene isomerization reaction, thus permitting feed of $C_8$ fractions which contain ethyl benzene without sacrifice of xylenes to conditions which will promote adequate conversion of ethyl benzene.

DESCRIPTION OF DRAWING

A plant suited to practice of the invention is illustrated in a diagrammatic flow-sheet in the single FIGURE of the annexed drawing.

SUMMARY OF THE INVENTION

The process of the invention utilizes a low acid catalyst, typified by zeolite ZSM-5 of low alumina content ($SiO_2/Al_2O_3$ of about 500 to 3000 or greater) and which may contain metals such as platinum or nickel. In using this less active catalyst the temperature is raised to 800° F. or higher for xylene isomerization. At these temperatures, ethyl benzene reacts primarily via dealkylation to benzene and ethane rather than via disproportionation to benzene and diethyl benzene and hence is strongly decoupled from the catalyst acid function. Since ethyl benzene conversion is less dependent on the acid function, a lower acidity catalyst can be used to perform the relatively easy xylene isomerization, and the amount of xylenes disproportionated is eliminated. The reduction of xylene losses is important because about 75% of the xylene stream is recycled in the loop resulting in an ultimate xylene loss of 6-10 wt. % by previous processes.

Since most of the ethyl benzene goes to benzene instead of benzene plus diethyl benzenes, the product quality of the new process is better than that of prior practices.

The new process also allows greater flexibility with respect to charge stock. Since ethyl benzene conversion is relatively independent of isomerization; high ethyl benzene containing charge stocks can be processed, which means that charge stocks from thermal crackers (about 30 wt. % ethyl benzene) can be used as well as conventional stocks from reformers. In addition, dealkylation of $C_2+$ alkyl groups is favored since the temperature is above 800° F. As a result, paraffins in the charge stock will not alkylate the aromatic rings eliminating xylene loss via this mechanism. Thus, this new process can process paraffins in the charge by cracking them to lighter paraffins eliminating the need for Udex Extraction. Finally, a small portion of the cracked fragments are recombined to form new aromatic rings which results in a net increase of aromatic rings.

DESCRIPTION OF SPECIFIC EMBODIMENTS

The foregoing objects and advantages are obtained in a plant corresponding to the flow sheet in the annexed drawing. The charge introduced by line 4 is a mixture of eight carbon atom alkyl aromatics, namely ethyl benzene and the three xylene isomers. Such charge stocks are derived from catalytic reformates, pyrolysis gasoline, etc. by distillation and solvent extraction to separate aromatic compounds from aliphatics. The present process has the ability, unique among xylene isomerization processes, of converting paraffins, olefins and the like which are separated by the normal distillation facilities of an isomerization loop. This process is therefore capable of accepting charge materials which contain substantial quantities (say up to 15%) of aliphatic hydrocarbons. Other sources for production of xylenes include toluene disproportionation and methylation of toluene. These charge stocks contain little or no ethyl benzene and therefore cannot take advantage of the novel ethyl benzene conversion feature of the invention. However, these are acceptable charge stocks alone or in combination with fractions which contain ethyl benzene. Such charge stock passes by line 4 to a xylene splitter column 5. The bottoms from the xylene splitter, constituted by o-xylene and $C_9$ aromatics passes by line 6 to the o-xylene tower 7 from which o-xylene is taken overhead at line 8 and heavy ends are removed by line 9. The overhead from xylene splitter column 5 is transferred to conventional crystallization separation 10 through line 11. The crystallizer operates in the manner described in Machell et al., U.S. Pat. No. 3,662,013 dated May 9, 1972.

Because it's melting point is much higher than that of the other $C_8$ aromatics, p-xylene is readily separated in the crystallizer after refrigeration of the stream and a xylene mixture lean in p-xylene is transferred to an isomerization unit through line 12. The isomerization charge passes through a heater 13, is admixed with hydrogen admitted through line 14 and the mixture is introduced to the reactor 15 operated in a manner presently to be described.

Isomerized product from reactor 15 is cooled in heat exchanger 16 and passes to a high pressure separator 17 from which separated hydrogen can be recycled in the process. The liquid product of the isomerization passes by line 18 to a stripper 19 from which light ends are passed overhead by line 20. The remaining liquid product constituted by $C_8+$ hydrocarbons is recycled in the system by line 21 to the inlet of xylene stripper column 5.

It will be seen that the system is adapted to produce maximum quantities of p-xylene from a mixed $C_8$ aromatic feed containing all of the xylene isomers plus ethyl benzene. The key to efficient operation for that purpose is in the isomerizer which takes crystallizer effluent lean in p-xylene and converts the other xylene isomers in part to p-xylene for further recovery at the crystallizer.

The reactor 15 contains a crystalline aluminosilicate (zeolite) catalyst of relatively low acid activity by reason of its very high silica/alumina ratio of 500 or higher. That catalyst, which is preferably combined with a metal from Group VIII of the Periodic Table promotes a reaction course which is unique at temperatures upwards of 800° F. Ethyl benzene in the charge is selectively cracked to benzene and ethane at little or no conversion of xylenes. The two conversions are, as noted above, decoupled such that, for the first time, reaction severity is not a compromise to achieve effective ethyl benzene conversion at "acceptable" loss of xylene. This characteristic of the process renders unnecessary the preliminary distillation to separate at least some of the ethyl benzene from the feed stream as practiced in prior processes. It has been further found that the present process has capability to convert paraffin hydrocarbons. This makes it possible to dispense with the expensive extraction step conventionally applied to the $C_8$ aromatic fraction of catalytically reformed naphthas in the manufacture and recovery of xylenes. In taking advantage of this feature, the feed stream at line 4 will contain the $C_8$ aromatics of a reformate or the like together with the paraffins of like boiling range, mostly nonanes. The paraffins in the charge are hydrocracked to lighter paraffins, including ethane, which will come off separator 17 with the recycle hydrogen in much greater quantity than that resulting from conversion of ethyl benzene. This requires modification of the usual techniques for maintaining concentration of the recycle hydrogen stream by withdrawal of a drag stream, not shown in the drawing.

The flow sheet of the drawing contemplates separate recovery of o-xylene. It will be immediately apparent that this isomer may be recycled in the system in the event o-xylene is not a desired product. In that event, splitter tower 5 is operated to take o-xylene overhead with the other $C_8$ aromatics and take only $C_9^+$ as bottoms from tower 5.

Particularly preferred are those zeolites having a constraint index within the approximate range of 1 to 12. Zeolites characterized by such constraint indices induce profound transformations of aliphatic hydrocarbons to aromatic hydrocarbons in commercially desirable yields and are generally highly effective in conversion reactions involving aromatic hydrocarbons. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 500; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methyl pentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |

| CAS | C.I. |
|---|---|
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperatures employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein as exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974, U.S. Pat. No. 4,046,859. This zeolite can be identified, in terms of mole ratios of oxides and in the anhydrous state, as follows:

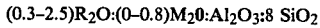
(0.3-2.5)R$_2$O:(0-0.8)M$_2$0:Al$_2$O$_3$:8 SiO$_2$ wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous states, as follows:

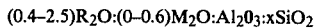
(0.4-2.5)R$_2$O:(0-0.6)M$_2$O:Al$_2$O$_3$:xSiO$_2$ wherein R is an organic nitrogen-containing cation derived from a 2-(hydroxyalkyl) trialkylammonium compound, wherein alkyl is methyl, ethyl or a combination thereof, M is an alkali metal, especially sodium, and x is 8 or more.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33 Å.

TABLE I

| d(Å) | I/Io |
|---|---|
| 9.8 ± 0.20 | Strong |
| 9.1 ± 0.19 | Medium |
| 8.0 ± 0.16 | Weak |
| 7.1 ± 9.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| | Broad | Preferred |
|---|---|---|
| R+/(R++M+) | 0.2-1.0 | 0.3-0.9 |
| OH-/SiO$_2$ | 0.05-0.5 | 0.07-0.49 |
| H$_2$O/OH- | 41-500 | 100-250 |
| SiO$_2$/Al$_2$O$_3$ | 8.8-200 | 12-60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH− is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days.

A more preferred temperature range is from about 150° C. to about 400° C. with the amount of time at a temperature in such range being from about 6 hours to about 80 days.

The digestion of the gel particles is carried out until the crystals form. The solid product is separated from the reaction medium, as by cooling the whole to room temperature, filtering and water washing. The crystalline product is thereafter dried, e.g., at 230° F. for from about 8 to 24 hours.

ZSM-35 is more particularly described in U.S. application Ser. No. 528,061, filed Nov. 29, 1974, U.S. Pat. No. 4,016,245. This zeolite can be identified, in terms of mole ratios of oxides and in the anhydrous state, as follows:

wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

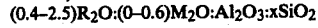

wherein R is an organic nitrogen-containing cation derived from ethylenediamine or pyrrolidine, M is an alkali metal, especially sodium, and x is greater than 8.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite pattersn exhibit a significant line at 11.33 Å. Close examination of some individual samples of ZSM-35 may show a very weak line at 11.3–11.5 Å. This very weak line, however, is determined not to be a significant line for ZSM-35.

TABLE II

| d(Å) | I/Io |
|---|---|
| 9.6 ± 0.20 | Very Strong-Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| | Broad | Preferred |
|---|---|---|
| $R^+/(R^+ + M^+)$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from pyrrolidine or ethylenediamine and M is an alkali metal ion, maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

ZSM-38 is more particularly described in U.S. Pat. No. 4,046,859, the entire contents of which are incorporated herein by reference.

A particularly preferred form of zeolite ZSM-5 is formed by crystallization of the zeolite from a solution containing metal ions, such as platinum as described in application Ser. No. 813,406 filed July 5, 1977, the entire contents of which are incorporated herein by reference.

The best results so far have been obtained with such ZSM-5 variants prepared by co-crystallization of metal and zeolite which are conveniently given the designation ZSM-5-(cc M), where M stands for the metal co-crystallized (cc) with the zeolite during synthesis. ZSM-5-(cc Pt) with 0.2–0.8 wt % Pt has proved particularly effective in the present process.

The crystalline structure of zeolite ZSM-5 (ccM) shows the following significant lines.

TABLE III

| 2θ | d(Å) | Relative Intensity |
|---|---|---|
| 7.90 | 11.2 ± 0.18 | VS |

TABLE III-continued

| 2θ | d(Å) | Relative Intensity |
|---|---|---|
| 3.79 | 10.1 ± 0.16 | S |
| 9.05 | 9.8 ± 0.16 | VW |
| 13.20 | 6.7 ± 0.11 | W |
| 13.90 | 6.4 ± 0.10 | W |
| 14.77 | 6.0 ± 0.10 | W |
| 15.00 | 5.92 ± 0.09 | VW |
| 15.52 | 5.71 ± 0.09 | VW |
| 15.87 | 5.58 ± 0.09 | W |
| 16.50 | 5.37 ± 0.09 | VW |
| 17.25 | 5.14 ± 0.08 | VW |
| 17.60 | 5.04 ± 0.08 | VW |
| 17.80 | 4.98 ± 0.08 | VW |
| 18.14 | 4.89 ± 0.08 | VW |
| 19.21 | 4.62 ± 0.07 | VW |
| 20.38 | 4.36 ± 0.07 | VW |
| 20.83 | 4.26 ± 0.07 | VW |
| 23.10 | 3.85 ± 0.06 | S-VS |
| 23.28 | 3.82 ± 0.06 | M |
| 23.76 | 3.76 ± 0.06 | W-W |
| 23.92 | 3.72 ± 0.06 | M-S |
| 24.29 | 3.66 ± | W-M |
| 23.92 | 3.72 ±W |  |
| 24.53 | 3.63 ± 0.06 | W |
| 24.78 | 3.59 ± 0.06 | VW |
| 24.54 | 3.49 ± 0.06 | VW |
| 25.85 | 3.45 ± 0.06 | VW |
| 26.18 | 3.40 ± 0.05 | VW |
| 26.57 | 3.35 ± 0.05 | VW |
| 26.97 | 3.31 ± 0.05 | VW |
| 27.38 | 3.26 ± 0.05 | VW |
| 27.58 | 3.23 ± 0.05 | VW |
| 28.09 | 3.18 ± 0.05 | VW |
| 28.38 | 3.14 ± 0.05 | VW |
| 29.13 | 3.06 ± 0.05 | VW |
| 29.40 | 3.04 ± 0.05 | VW |
| 29.90 | 2.99 ± 0.05 | W |
| 30.22 | 2.96 ± 0.05 | VW |
| 30.55 | 2.93 ± 0.05 | VW |
| 31.15 | 2.87 ± 0.05 | VW |

These values were determined by standard techniques. The radiation was the K-alpha doublet copper, and a scintillation counter spectrometer with a strip chart pen recorder was used. The peak heights, I, and the positions as a function of 2 times theta, were theta is the Bragg angle, were read from the spectrometer chart. From these, the relative intensities, 100 I/Io, where $I_o$ is the intensity of the strongest line or peak, and d (obs.), the interplanar apacing in A, corresponding to the recorded lines, were calculated. In Table III the relative intensities are given in terms of a subjective evaluation. It should be understood that this X-ray diffraction pattern is characteristic of all the species of ZSM-5 (ccM) compositions. Ion exchange of the sodium ion with cations reveals substantially the same pattern with some minor shifts in interplanar spacing and variation in relative intensity. Other minor variations can occur depending on the silica to alumina ratio of the particular sample and the extent of thermal conditioning.

ZSM-5 (ccm) can be prepared from a reaction mixture having a composition, in terms of mole ratios of oxides, falling within the following ranges:

TABLE IV

|  | Broad | Preferred | Most Preferred |
|---|---|---|---|
| OH⁻/SiO₂ | 0.07–1.0 | 0.1–0.8 | 0.2–0.75 |
| R₄N⁺/(R₄N⁺+ Na⁺) | 0.2–0.95 | 0.3–0.9 | 0.4–0.9 |
| H₂O/OH⁻ | 10–300 | 10–300 | 10–300 |
| SiO₂/Al₂O₃ | 30–3000 | 70–1000 | 70–500 |
| Other metal, Wt. % | 0.005–5 | 0.01–1 | 0.1–1.0 |

Typical reaction conditions consist of heating the foregoing reaction mixture to a temperature of from about 100° C. to 175° C. for a period of time of from about six hours to 120 days. A more preferred temperature range is from about 95° C. to 175° C. with the amount of time at a temperature in such range being from about 12 hours to 8 days.

The digestion of the gel particles is carried out until crystals form. The solid product is separated from the reaction medium, as by cooling the whole to room temperature, filtering and water washing.

The foregoing product is dried, e.g. at 230° F., for from about 8 to 24 hours. Of course, milder conditions may be employed if desired, e.g. room temperature under vacuum.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicate are ZSM-5, ZSM-11, ZSM-12, ZSM-38, ZSM-35, and ZSM-5 (ccM), with ZSM-5 and ZSM-5 (ccM) particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to alumina ratio of at least about 500 and a dried crystal density of not less than about 1.6 grams per cubic centimeter. The dry density for known structures may be calculated from the number of silicon plus aluminum atoms per 1000 cubic Angstroms, as given, e.g. on page 19 of the article on Zeolite Structure by W.M. Meier. This paper, the enire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pykometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chebazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

EXAMPLE 1

Zeolite ZSM-5 (cc Pt) having a silica to alumina ratio of 660 and containing 0.23% by weight of platinum was prepared for use in accordance with this invention.

The following reactants were heated together:

| Water | 710 grams |
|---|---|
| Chloroplatinic acid (40 wt. % Pt) | 3 |
| Hydrochloric acid | 35 |
| Tetraethyl Ammonium Bromide | 25 |
| Water Glass | 290 |
| 8.9% Na$_2$O | |
| 28.7% SiO | |
| 62.4% H$_2$O | |
| 0.046% Al$_2$O$_3$ | |

The product contained 0.23% platinum in zeolite of 660 silica/alumina.

EXAMPLE 2

Zeolite ZSM-5 (cc Pt) having a silica to alumina ratio of 1041 and containing 0.76% by weight of platinum was prepared for use in accordance with the invention.

The following reactants were heated together:

| Water | 600 grams |
|---|---|
| Tetrapropylammonium bromide | 100 |
| Chloroplatinic acid (40 wt. % Pt) | 3 |
| Al$_2$(SO$_4$)$_3$ . 14 H$_2$O | 0.77 |
| Tetraethyl orthosilicate | 314 |
| 50% NaOH solution | 21.2 |

After crystallization was complete, the crystals were separated by filtration, washed with water, dried, base exchanged with ammonium cation and calcined at about 1000° F. The resultant catalyst had a silica/alumina ratio of 1041 and contained 0.76 wt. % platinum.

EXAMPLE 3

A mixture of hydrocarbons was prepared which simulates charge to the isomerizer 15 in an operation charging at line 4 of the drawing, a fraction prepared by distillation from catalytic reformate to include the C$_8$ aromatics. The simulated charge contained 6.9% n-nonane, 30.7% ethyl benzene and 62.4% of a mixture of xylenes poor in p-xylene, viz. 73.3% m-xylene, 17.8% o-xylene and 8.9% p-xylene. That mixture was reacted over the catalyst of Example 1. Reaction conditions and products of the reaction are tabulated in Table V.

EXAMPLE 4

The same charge as in Example 3 was processed over the catalyst of Example 2, with results as shown in Table V.

EXAMPLE 5

A simulated charge was prepared by blending 9.8% ethyl benzene with 90.2% of mixed xylenes having the composition set out in Example 3. That charge approximates the isomerizer feed in a system supplied with fresh feed prepared by fractionation of catalytic reformate to separate a $C_8$ aromatics cut and solvent extraction to reject the paraffin content of the fraction. Results are shown in Table V on processing the simulated charge over the catalyst of Example 2.

TABLE V

Conversion of Simulated Charge Over ZSM-5 (cc Pt) at 900° F., 200 psig, 5 mols $H_2$ Per Mole of Hydrocarbon

| Example No. | | 3 | 4 | | 5 |
|---|---|---|---|---|---|
| Silica/alumina | | 660 | 1041 | | 1041 |
| Pt. % by weight | | 0.23 | 0.76 | | 0.76 |
| WHSV | | 10 | 4 | | 4 |
| Material Balance | | 97.31 | 98.74 | | 100.27 |
| Hours on stream | | 95 | 24 | | 87 |
| Wt. % | | | | | |
| $C_2$'s PAR | | 5.50 | 5.28 | | 1.42 |
| $C_3$'s PAR | | 1.66 | 1.53 | | 0.04 |
| $C_4$'s PAR | | 1.35 | 1.29 | | 0.01 |
| $C_5$'s PAR | | 1.36 | 1.37 | | 0.07 |
| $C_6$'s PAR | | 0.35 | 0.29 | | 0.01 |
| Benzene | | 13.53 | 13.01 | | 2.97 |
| $C_7$s PAR | | 0.01 | 0.01 | | — |
| Toluene | | 0.90 | 0.81 | | 0.57 |
| $C_8$s PAR | | 0.02 | 0.01 | | — |
| | Charge | | | Charge | |
| Ethyl bezene | 30.7 | 11.40 | 12.29 | 9.8 | 5.10 |
| m-xylene | 45.7 | 35.06 | 36.03 | 66.1 | 50.38 |
| p-xylene | 5.6 | 14.16 | 13.14 | 8.0 | 19.92 |
| o-xylene | 11.1 | 12.70 | 13.05 | 16.1 | 19.10 |
| $C_9$PAR | 6.9 | 1.30 | 1.42 | | — |
| $C_9$ AR | | 0.23 | 0.21 | | 0.41 |
| $C_{10}$ + AR | | 0.26 | 0.25 | | 0.05 |
| Wt. % Conversion | | | | | |
| Ethyl Benzene | | 62.86 | 60.46 | | 47.96 |
| Wt. % Conversion $C_9$ | | 81.59 | 79.42 | | |
| Mole $C_6H_6$/Mole Ethyl | | | | | |
| Benzene Reacted | | 0.95 | 0.96 | | 0.86 |

It will be noted from the experimental data in Table V that reactions of ethyl benzene are predominantly by conversion to benzene as contrasted with disproportionation reactions which yield diethyl benzene. Although it is known that diethyl benzene can be reacted to chemical raw materials having a present market value as such, in practice the diethyl benzene is diverted to fuel use in motor gasoline and the like. The present process yields benzene as the heavily predominant product to the significant economic advantage of the overall process. It has been demonstrated that the conditions (catalyst, temperature) induce dealkylation of ethyl benzene by charging ethyl benzene alone. There are indications that dealkylation of ethyl benzene in the presence of xylene has a favorable effect on selectivity of conversion of ethyl benzene to benzene. The data are not adequate to establish a true "cause and effect" relationship but the trend of data do indicate that the ethyl benzene conversion is more selective for benzene as product when xylenes are present, despite the observed lack of the usual relationship of coupling wherein degree of xylene conversion to other compounds (xylene loss) tends in the same direction as ethyl benzene conversion.

The reaction is found to proceed in the direction indicated with metal free high silica zeolite, but is less selective than when the zeolite is associated with a metal of Group VIII. Also shorter catalyst life is to be expected with metal-free zeolite catalyst. Particularly preferred are the noble metals of Group VIII, namely platinum, palladium, osmium, iridium, ruthenium and rhodium. The other Group VIII metals, such as nickel exhibit the advantages of the invention to less extent, in some cases by minor increase of xylene loss at conditions to promote increased ethyl benzene conversion, some apparent coupling of the reactions.

The metal should be a minor component of the catalyst, say 0.05 to 2.0 weight percent and is preferably highly dispersed. For purposes of achieving dispersion of metal, the catalyst is preferably of the ZSM-5 (ccM) variety wherein the metal is present in the forming solution from which the zeolite is synthesized. When metal is applied to a fully formed zeolite, as by impregnation with conventional techniques, care must be exercised. The quantity of metal should be relatively low, say up to 0.2 weight percent. At moderate to high metal content, e.g. 0.3 to 1.0 weight percent platinum, applied by impregnation the catalyst exhibits tendency to loss of benzene rings, apparently by hydrocracking, possibly on relatively large crystals of metal within the pores of the catalyst. There problems are largely alleviated when the metal-bearing zeolite is of the ZSM-5 (ccM) variety and all the metal content is derived from metal compounds in the synthesis liquor.

EXAMPLE 6

Catalyst comprising 0.18 wt. % platinum in zeolite ZSM-5 (cc Pt) of 2000 silica/alumina ratio was prepared from the reaction mixture:

| | | |
|---|---|---|
| Water | 600 | grams |
| Tetrapropyl Ammonium Bromide | 100 | |
| Chloroplatinic Acid (40 wt. % Pt) | 1 | |
| Tetraethyl Orthosilicate | 314 | |
| $Al_2(SO_4)_3 \cdot 14 H_2O$ | 0.38 | |
| Sodium Hydroxide | | |

| | |
|---|---|
| -continued | |
| (50% NaOH) | 21.2 |

EXAMPLE 7

Zeolite HZSM-5 of 1000 silica/alumina ratio was prepared from the following mixture:

| | | |
|---|---|---|
| Water | 600 | grams |
| Tetrapropyl Ammonium Bromide | 100 | |
| $Al_2(SO_4)_3 \cdot 14 H_2O$ | 0.76 | |
| Tetraethyl Ortho-silicate | 314 | |
| Sodium Hydroxide (50% NaOH) | 21.2 | |

Following conversion to the hydrogen form by ammonium base exchange and calcining, portions of the zeolite were impregnated with 0.4 weight percent platinum. A further ZSM-5 catalyst was prepared by impregnation of zeolite having 1600 silica/alumina ratio with 4.0 weight percent nickel, blending with 35 weight percent alumina and extrusion.

EXAMPLES 8-11

Catalyst prepared according to Examples 6 and 7 were employed in processing ethyl benzene mixed with xylene in which the distribution of isomers was as described in Example 3. Conditions and results obtained are summarized in Table VI.

TABLE VI

| | Conversion of Ethyl Benzene/Xylene Mixtures | | | |
|---|---|---|---|---|
| Example No. | 8 | 9 | 10 | 11 |
| Charge, Wt. % | | | | |
| Ethyl Benzene | 10 | 9.8 | 9.8 | 10.4 |
| Xylene | 89.5 | 90.2 | 90.2 | 89.5 |
| $C_9$ | 0.1 | — | — | 0.1 |
| Catalyst | | | | |
| Zeolite | ZSM-5 (ccPt) | ZSM-5 | ZSM-5 | ZSM-5 |
| Metal | 0.18% Pt | 0.04% Pt | None | 4.0% Ni |
| Temperature (° F.) | 900 | 900 | 900 | 900 |
| Pressure (psig) | 200 | 200 | 200 | 200 |
| WHSV | 5 | 10 | 5 | 10 |
| $H_2$/HC | 5 | 5 | 5 | 5 |
| Material Balance | 96.49 | 100.01 | 99.39 | 98.08 |
| Hours on Stream | 3 | 6 | 2 | 43 |
| Wt. % | | | | |
| $C_2$'s PAR | 0.47 | 0.56 | 0.96 | 1.50 |
| $C_3$'s PAR | 0.03 | 0.02 | 0.03 | 0.01 |
| $C_4$'s PAR | 0.01 | | 0.01 | 0.01 |
| $C_5$'s PAR | 0.02 | 0.01 | 0.02 | 0.01 |
| $C_6$'s PAR | | | | 0.02 |
| Benzene | 3.03 | 2.16 | 2.74 | 4.39 |
| Toluene | 0.54 | 0.42 | 0.56 | 1.29 |
| $C_9$'s PAR | 0.01 | 0.01 | 0.02 | 0.10 |
| Ethyl Benzene | 5.99 | 6.37 | 5.42 | 4.18 |
| m-Xylene | 48.04 | 49.08 | 47.78 | 45.93 |
| p-Xylene | 21.20 | 20.57 | 20.05 | 20.17 |
| o-Xylene | 19.40 | 20.29 | 20.96 | 20.43 |
| $C_9$ PAR | 0.05 | | 0.08 | |
| $C_9$ AR | 0.49 | 0.38 | 0.50 | 1.19 |
| $C_{10}$ + AR | 0.12 | 0.15 | 0.29 | 0.78 |
| Wt. % Conversion Ethyl benzene | 40.10 | 35.00 | 44.69 | 59.81 |
| Mole $C_6H_6$/Mole Ethyl Benzene Reacted | 1.02 | 0.86 | 0.85 | 0.96 |

We claim:

1. In a process for isomerizing the xylene content of a charge mixture of eight carbon atom aromatic hydrocarbon compounds which mixture contains xylene and ethyl benzene by contact at conversion conditions with a catalyst comprising a zeolite having a silica/alumina ratio greater than 12 and a constraint index of 1 to 12, the improvement resulting in conversion of ethyl benzene to benzene which comprises using as said catalyst a zeolite having a silica/alumina ratio of at least 500 maintaining a conversion temperature of about 800° F. to about 1000° F.

2. A process according to claim 1 wherein said zeolite is ZSM-5 (ccM).

3. A process according to claim 1 wherein said zeolite is ZSM-5.

4. A process according to claim 1 wherein said catalyst also comprises a metal of Group VIII of the Periodic Table.

5. A process according to claim 4 wherein said zeolite is ZSM-5 (ccPt).

6. A process according to claim 4 wherein said zeolite is ZSM-5.

7. A process according to claim 4 wherein said charge mixture is admixed with hydrogen.

8. A process according to claim 7 wherein said zeolite is ZSM-5 (ccM).

9. A process according to claim 7 wherein said zeolite is ZSM-5.

10. A process according to claim 1 wherein the reaction temperature is 800°-1000° F.

11. A process according to claim 1 resulting in conversion of ethyl benzene to benzene at substantially no loss of xylene in the product as compared to the charge.

12. A process according to claim 1 wherein the said charge mixture contains paraffin hydrocarbons.

13. A process according to claim 1 wherein the said charge mixture consists essentially of aromatic hydrocarbons.

* * * * *

UNITED STATES PATENT AND TRADEMARK OFFICE
CERTIFICATE OF CORRECTION

PATENT NO. : 4,163,028
DATED : July 31, 1979
INVENTOR(S) : SAMUEL A. TABAK and ROGER A. MORRISON It is certified that error appears in the above-identified patent and that said Letters Patent are hereby corrected as shown below:

Column 1, line 33, delete "W-M"
Column 1, line 34, delete "23.92  3.72+0.06"
Column 2, line 59, after word "possible" insert word "then"
Column 3, line 26, "in a diagrammatic" should read --as a diagrammatic--
Column 7, line 39, "as exemplified" should read --is exemplified--
Column 8, line 16, "7.1 + 9.14" should read --7.1 + 0.14--

Column 11, line 19, --WM-- should be inserted in Column 3
Column 11, line 20, delete "W-W"
Column 11, line 22, "24.29 3.66+" should be --24.29--, --3.66 + 0.06-- and --W--
Column 11, line 23, delete "W-M"
Column 11, line 24, delete "23.92 3.72 + W"
Column 11, line 43, "were theta" should be --where theta--
Column 11, line 60, "(ccm)" should be --(ccM)--
Column 13, line 28, "Chebazite" should be --Chabazite--
Column 15, Table V, line 17, "C7s PAR" should be --$C_7$'s PAR--
Column 15, Table V, line 19, "C8s PAR" should be --$C_8$'s PAR--

Signed and Sealed this

Fifteenth Day of January 1980

[SEAL]

Attest:

SIDNEY A. DIAMOND

Attesting Officer    Commissioner of Patents and Trademarks